(12) United States Patent
Coates et al.

(10) Patent No.: US 6,899,735 B2
(45) Date of Patent: May 31, 2005

(54) MODULAR INTERVERTEBRAL PROSTHESIS SYSTEM

(75) Inventors: Bradley J. Coates, Rossville, TN (US); James E. Van Hoeck, Cordova, TN (US); T. Andrew Simonton, Germantown, TN (US); Regis Haid, Atlanta, GA (US); Kevin Foley, Germantown, TN (US)

(73) Assignee: SDGI Holdings, Inc., Wilmington, DE (US)

( * ) Notice: Subject to any disclaimer, the term of this patent is extended or adjusted under 35 U.S.C. 154(b) by 208 days.

(21) Appl. No.: 10/263,115

(22) Filed: Oct. 2, 2002

(65) Prior Publication Data

US 2004/0068318 A1 Apr. 8, 2004

(51) Int. Cl.⁷ ................................................. A61F 2/44
(52) U.S. Cl. ................................. 623/17.16; 623/17.11
(58) Field of Search ........................... 623/17.11, 17.15, 623/17.16

(56) References Cited

U.S. PATENT DOCUMENTS

| | | |
|---|---|---|
| 4,759,709 A | 7/1988 | Luken, Jr. et al. |
| 4,805,602 A | 2/1989 | Puno et al. |
| 5,002,576 A | 3/1991 | Fuhrmann et al. |
| 5,005,562 A | 4/1991 | Cotrel |
| 5,176,678 A | 1/1993 | Tsou |
| 5,236,460 A | 8/1993 | Barber |
| 5,258,031 A | 11/1993 | Salib et al. |
| 5,370,697 A | 12/1994 | Baumgartner |
| 5,425,773 A | 6/1995 | Boyd et al. |
| 5,458,641 A | 10/1995 | Ramirez Jimenez |
| 5,458,642 A | 10/1995 | Beer et al. |
| 5,534,029 A * | 7/1996 | Shima ..................... 623/17.15 |
| 5,556,431 A | 9/1996 | Büttner-Janz |
| 5,562,738 A | 10/1996 | Boyd et al. |
| 5,674,296 A | 10/1997 | Bryan et al. |
| 5,865,846 A | 2/1999 | Bryan et al. |
| 5,899,901 A | 5/1999 | Middleton |
| 6,019,792 A | 2/2000 | Cauthen |
| 6,106,557 A * | 8/2000 | Robioneck et al. ...... 623/17.15 |
| 6,113,637 A | 9/2000 | Gill et al. |
| 6,146,421 A * | 11/2000 | Gordon et al. ........... 623/17.15 |
| 6,179,874 B1 | 1/2001 | Cauthen |
| 6,375,683 B1 * | 4/2002 | Crozet et al. ............ 623/17.15 |
| 6,419,706 B1 | 7/2002 | Graf |
| 6,440,168 B1 | 8/2002 | Cauthen |
| 6,517,580 B1 * | 2/2003 | Ramadan et al. ......... 623/17.15 |
| 6,579,290 B1 * | 6/2003 | Hardcastle et al. ........... 606/61 |

(Continued)

FOREIGN PATENT DOCUMENTS

| | | |
|---|---|---|
| EP | 0 699 426 | 3/1996 |
| FR | 2 718 635 | 10/1995 |
| FR | 2 805 457 | 8/2001 |
| WO | WO 99/65412 | 12/1999 |

*Primary Examiner*—Pedro Philogene
*Assistant Examiner*—D. Austin Bonderer
(74) *Attorney, Agent, or Firm*—Coats & Bennett, P.L.L.C.

(57) ABSTRACT

A modular intervertebral prosthesis system includes first and second baseplates and an insert designed to mate to the baseplates. The baseplates include a mounting section and a intervertebral section extending away from the mounting section generally perpendicular thereto. The intervertebral section has at least one aperture passing therethrough. When installed, the insert is disposed between the intervertebral sections of the baseplates and faces the apertures. In this way, the insert is not insulated from the vertebral members, thereby allowing for osteoinduction, osteoconduction, and/or osteointegration, if desired. The insert may take the form of an articulating-type insert or a fusion-type insert, with the baseplates being operative with both types of inserts. After installation of the insert between the baseplates, the insert may be readily removed, at least initially.

58 Claims, 4 Drawing Sheets

U.S. PATENT DOCUMENTS

| | | | |
|---|---|---|---|
| 6,579,320 B1 * | 6/2003 | Gauchet et al. | 623/17.15 |
| 6,610,093 B1 * | 8/2003 | Pisharodi | 623/17.15 |
| 6,648,917 B2 * | 11/2003 | Gerbec et al. | 623/17.11 |
| 6,682,561 B2 * | 1/2004 | Songer et al. | 623/17.11 |
| 2003/0187506 A1 * | 10/2003 | Ross et al. | 623/17.13 |
| 2003/0204261 A1 * | 10/2003 | Eisermann et al. | 623/17.14 |
| 2004/0030387 A1 * | 2/2004 | Landry et al. | 623/16.11 |
| 2004/0034423 A1 * | 2/2004 | Lyons et al. | 623/17.13 |
| 2004/0049270 A1 * | 3/2004 | Gewirtz | 623/17.11 |
| 2004/0073314 A1 * | 4/2004 | White et al. | 623/17.15 |
| 2004/0102846 A1 * | 5/2004 | Keller et al. | 623/17.11 |
| 2004/0133278 A1 * | 7/2004 | Marino et al. | 623/17.14 |

* cited by examiner

MODULAR INTERVERTEBRAL PROSTHESIS SYSTEM

BACKGROUND

In the treatment of diseases, injuries or malformations affecting spinal motion segments, and especially those affecting disc tissue, it has long been known to remove some or all of a degenerated, ruptured or otherwise failing disc. In cases involving intervertebral disc tissue that has been removed or is otherwise absent from a spinal motion segment, corrective measures are indicated to insure the proper spacing of the vertebrae formerly separated by the removed disc tissue. Sometimes, the two adjacent vertebrae are fused together using transplanted bone tissue, an artificial fusion component, or other compositions or devices. Other times, different types of intervertebral disc arthroplasty devices have been employed to prevent the collapse of the intervertebral space between adjacent vertebrae while maintaining a certain degree of stability and range of pivotal and rotational motion therebetween. Such devices typically include two or more articular components that are attached to respective upper and lower vertebrae. The articular components are anchored to the upper and lower vertebrae by a number of methods, including the use of bone screws that pass through corresponding openings in each of the elements and thread into vertebral bone, and/or by the inclusion of spikes or teeth that penetrate the vertebral endplates to inhibit migration or expulsion of the device. The articular components are typically configured to allow the elements, and correspondingly the adjacent vertebrae, to pivot and/or rotate relative to one another.

However, it is not always possible to determine a priori whether a fusion approach or an articulating joint approach is appropriate for a given situation. Further, it may be necessary to change the type or size of the articulating joint, and/or to change from an articulating joint to a fusion joint, after a first articulating joint has been installed. As such, there remains a need for intervertebral prosthesis systems that address one or more of these problems.

SUMMARY

The present invention relates generally to a modular intervertebral prosthesis system and a method of using the same. While the actual nature of the invention covered herein can only be determined with reference to the claims appended hereto, certain forms of the invention that are characteristic of embodiments disclosed herein are described briefly as follows.

One embodiment of the modular intervertebral prosthesis system of the present invention includes first and second baseplates and an insert designed to mate to the baseplates. The baseplates include a mounting section and an intervertebral section extending away from the mounting section such that the baseplates have a generally L-shaped side profile. The intervertebral section has at least one aperture passing therethrough. When installed, the insert is disposed between the intervertebral sections of the baseplates, and faces the apertures. In this way, the insert is not insulated from the vertebral members, thereby allowing for osteoinduction and/or osteoconduction and/or osteointegration, if desired. The insert may take the form of an articulating-type insert or a fusion-type insert, with the baseplates being operative with both types of inserts.

After installation of the insert between the baseplates, the insert may be readily removed, so as to allow the surgeon to try another size or type of insert during the same surgery without removing the baseplates from the vertebral members. In addition, if the insert has not fused to the vertebral members, the insert may be removed during a later surgery to allow for replacement of the insert, or substitution of another type of insert.

DETAILED DESCRIPTION

Referring to FIGS. 1–6, the modular prosthesis system of the present invention, generally indicated at 10, includes two baseplates 20 and at least one insert 70. In some embodiments, the system 10 comprises more than one insert 70. The baseplates 20 include a mounting section 30 for mounting to a vertebral member 4,6 and an intervertebral section 50 that is intended to be disposed substantially between the two vertebral members 4,6. The mounting section 30 may be a rigid, generally planar section. In one embodiment, mounting section 30 has a slight curve to conform with the patient's anatomy (see FIG. 5). The mounting section 30 includes two spaced apart countersunk screw holes 32 for receiving mounting screws 40a that mount the baseplate 20 to the respective vertebral member 4,6. Between the two screw holes 32 is a smaller hole 36 for a locking screw 40b or other locking mechanism, such as a snap, etc. The area around hole 36 may advantageously be slightly recessed so as to accept an associated retaining ring 37 as discussed below. In addition, the edge of the mounting section 30 closest to the intervertebral section 50 may advantageously include a notch 34 for a corresponding tab 74 on an insert 70, as described more fully below. The portion of the mounting section 30 near where the intervertebral section joins the mounting section 30 may include shoulder sections 38 if desired for added strength.

Figure 1:
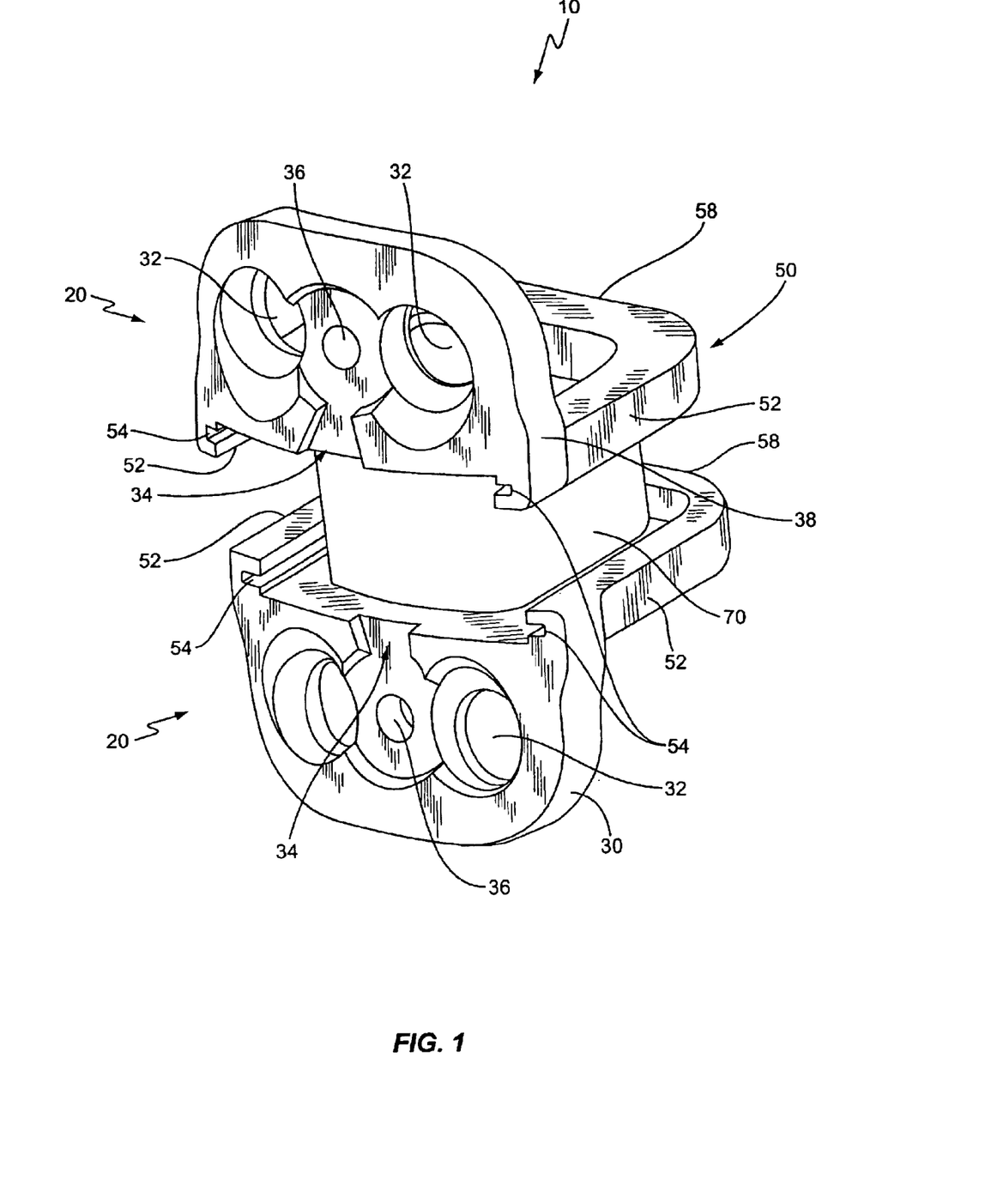
FIG. 1 is a perspective view of one embodiment of the prosthesis system in accordance with the present invention.
Figure 2:
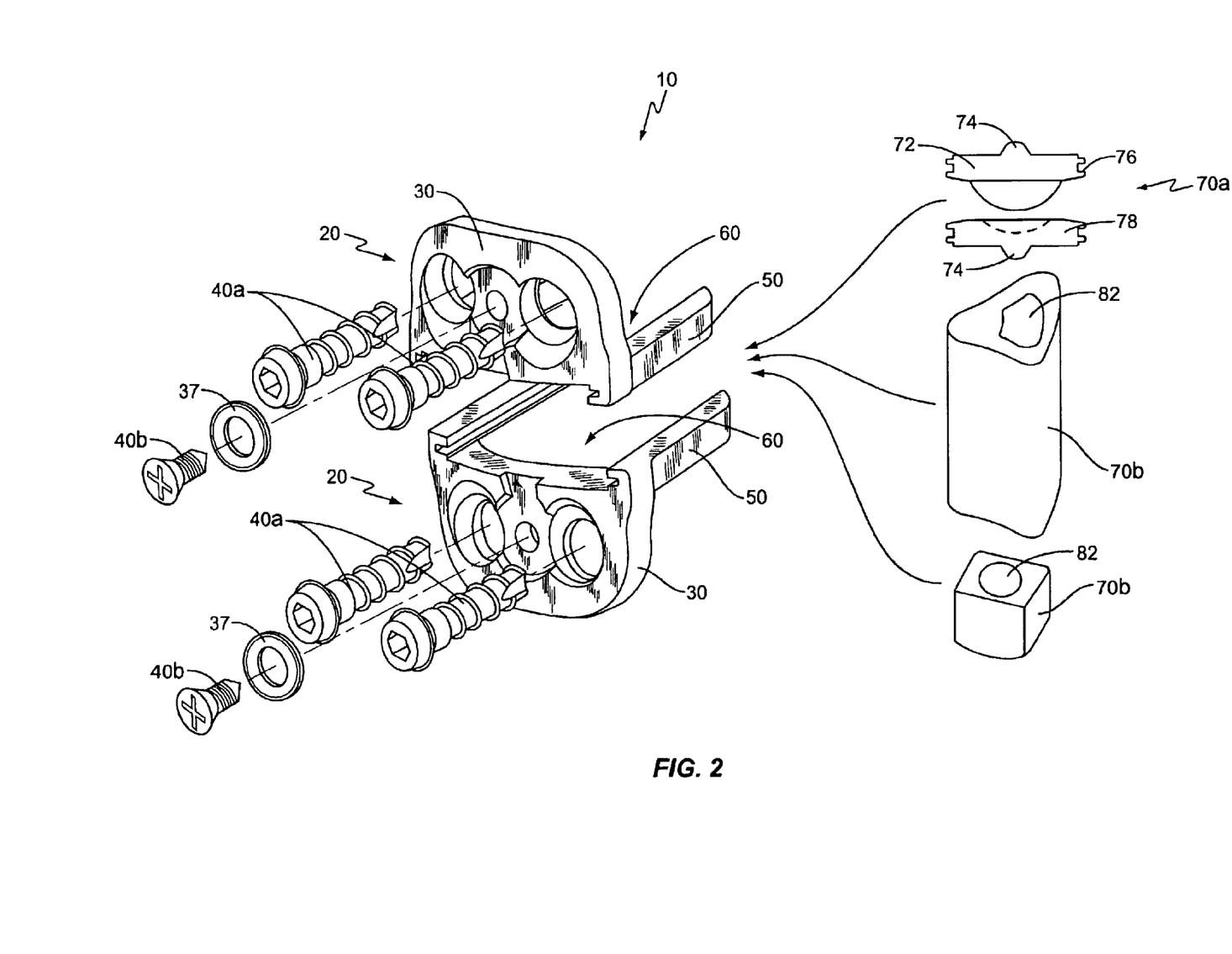
FIG. 2 is a partially exploded view of another embodiment of the prosthesis system in accordance with the present invention.
Figure 3:
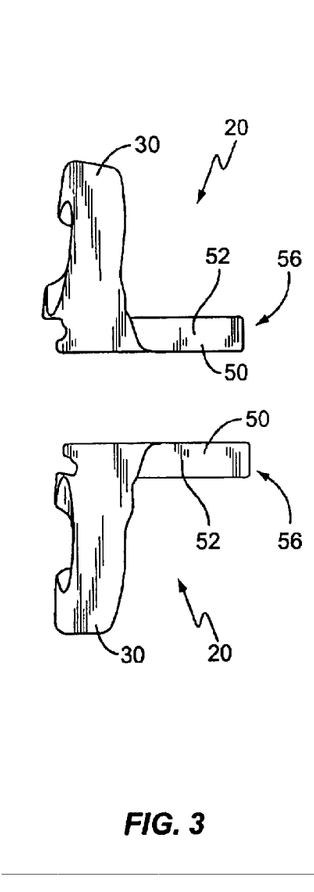
FIG. 3 is a side view of the baseplates of FIG. 2.
Figure 4:
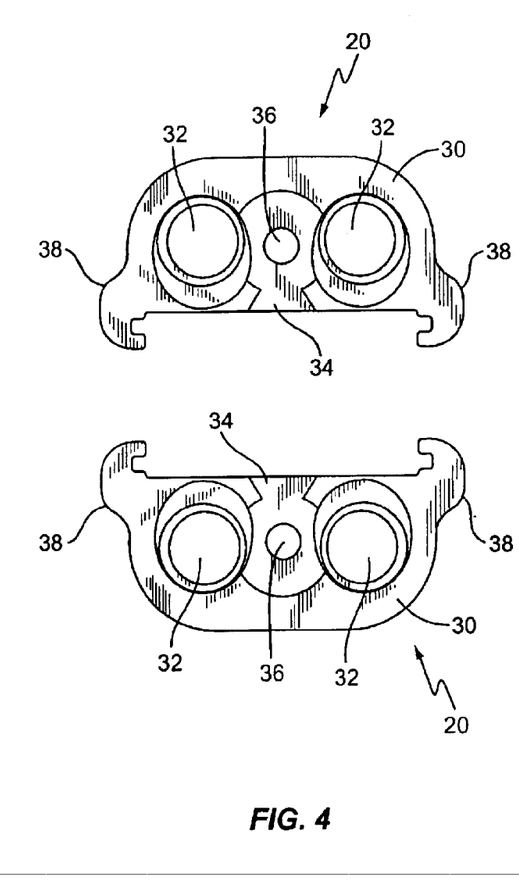
FIG. 4 is a front view of the baseplates of FIG. 3.
Figure 5:
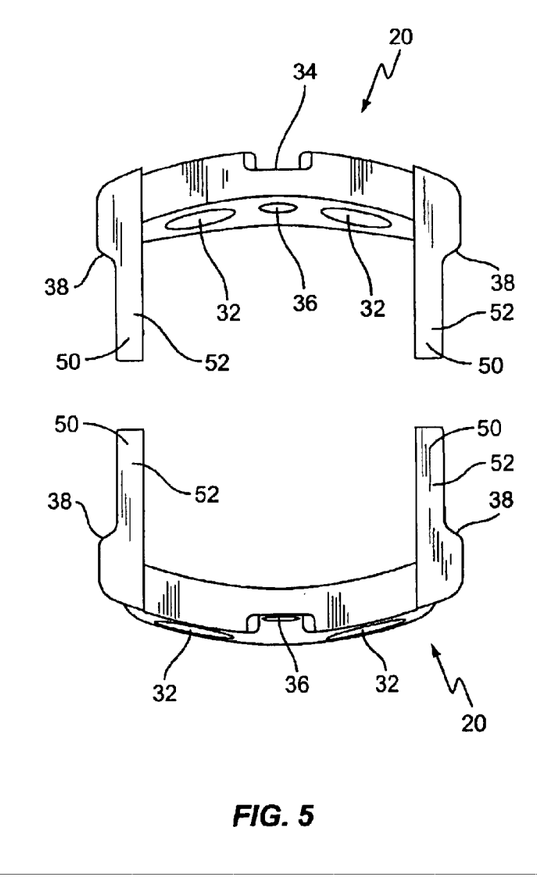
FIG. 5 is a bottom view of the baseplates of FIG. 3.

The intervertebral section 50 may extend away from the mounting section 30 so that the baseplate 20 has a L-shaped side profile (see FIG. 3). Indeed, the intervertebral section 50 may advantageously extend away from the mounting section 30 in a generally perpendicular (i.e., 90°±20°) fashion. The intervertebral section 50 includes an aperture 60 that extends through the intervertebral section 50 (e.g., from the inferior side to the superior side). The aperture 60 may take the form of a hole, or may be simply the space between two arms 52 that extend out from the mounting section 30 (see FIGS. 2, 5). The arms 52 may advantageously include grooves 54 on their interior sides, for engaging corresponding rails 76 on some insert designs, as discussed below. The distal ends of the arms 52 may optionally be bridged by a linking bridge member 58 (see FIG. 1), such that the aperture 60 is bounded on all sides when viewed from above. While the two baseplates 20 may be different, the baseplates 20 may advantageously be substantially identical so as to be interchangeable.

One advantage of the prosthesis system 10 shown in FIGS. 1–5 is that it may employ a variety of inserts 70. For instance, the baseplates 20 may be used with one version of an articulating joint, such as the ball and trough arrangement 70a shown in FIG. 2. Such ball and trough insert arrangements may include two principle parts, with one part 72 having a ball shape and one part 78 having a corresponding hollow (or trough). The two portions 72,78 of the articulating type insert 70a are designed to slide into the corresponding baseplates 20. As pointed out above, the inserts 70a may have rails 76 on their sides for engaging the grooves 54 in the baseplates 20, for purposes of alignment and/or stabilization. In addition, one edge of each part 72,78 of the articulating insert 70a may include a tab 74 that co-operates with the notch 34 on the corresponding baseplates 20 to prevent over-insertion with respect to the baseplates 20, and to aid in securing the insert 70 to the baseplate 20. Reference is made to U.S. patent application Ser. No. 10/042,589 entitled "Artificial Disc Implant," filed Jan. 9, 2002, U.S. Provisional Application No. 60/375,354 entitled "Articular Disc Prosthesis And Method For Implanting The Same," filed Apr. 25, 2002, and U.S. Pat. No. 6,113,637 entitled "Artificial Intervertebral Joint Permitting Translational And Rotational Motion," all incorporated herein by reference, for additional details concerning design of the ball and trough surfaces. Of course, other forms of inserts 70 may also be employed to form an articulating joint in association with the baseplates 20, with the particular details being unimportant other than the ability to connect to the baseplates 20. For instance, an insert 70 based on a single flexible member, an enclosed ball-and-socket, a hinge, or the like may be used without departing from the broadest forms of the present invention.

In one embodiment, the articulating type inserts 70a are removable from the baseplates 20 once installed. For the embodiments shown in FIGS. 1–5, the insert parts are secured in place via retaining ring 37, screw 40b, and threaded hole 36, with the outer diameter of the retaining ring 37 being large enough to overlap the tab 74 on the insert parts 72,78 and hold tab 74 in notch 34 and against the mounting section 30 of the corresponding baseplate 20. Once installed, the insert parts 72,78 may be readily removed for inspection and/or replacement by simply removing screw 40b and retaining ring 37, and then sliding the insert parts 72,78 out from their respective baseplates 20. The insert parts 72,78 may, if desired, be replaced with insert parts 72,78 of another size and/or design, or an insert of a different type, such as insert 70b. Note, however, that care should be taken when replacing or otherwise removing the articulating type insert 70a to take into account any osteointegration that may have taken place between the bone and the insert 70a, particularly through the apertures 60.

As an alternative to the articulating type inserts 70a discussed above, the insert 70 may be of a type known as "fusion" inserts 70b. For example, the insert 70b may comprise a portion of precision milled allograft bone harvested from a cadaver, a portion of autograft bone harvested from the same patient, or some synthetic material. One example of a commercially available product that may be used as a fusion-type insert 70b is sold under the trademark "CORNERSTONE" by Medtronic Sofamor Danek of Memphis, Tenn. In one embodiment, the insert 70b includes a central passage that extends 82 from one end to the other of the insert 70b. When the insert 70b is positioned between the baseplates 20, the passage 82 faces the apertures 60 in the baseplates 20, thereby providing a direct path from the vertebral member 4,6 to the fusion insert 70b, so as to promote osteoinduction and osteoconduction.

The baseplates 20 should be made from a suitable rigid material, such as stainless steel, various titanium alloys known in the art, cobalt-chrome-molybdenum alloys ASTM F-799 or F-75, or any other metallic alloy known in the art. The articulating type inserts 70a may also be made from metallic alloys, but may also include suitable plastic and/or ceramic materials as desired. The fusion inserts 70b may be made from actual bone material, demineralized bone matrix, ceramics (e.g., hydroxy apatite), polymers (e.g., polyetheretherketone bioinert polymer (PEEK)), or any other suitable material, including bioresorbable materials. Indeed, the fusion inserts 70b may be made from, or filled with, bone growth inducing materials, such as a sponge, matrix, and/or other structural carrier impregnated with a protein such as bone morphogenic protein (BMP), LIM mineralization protein (LMP), etc.

Figure 6:
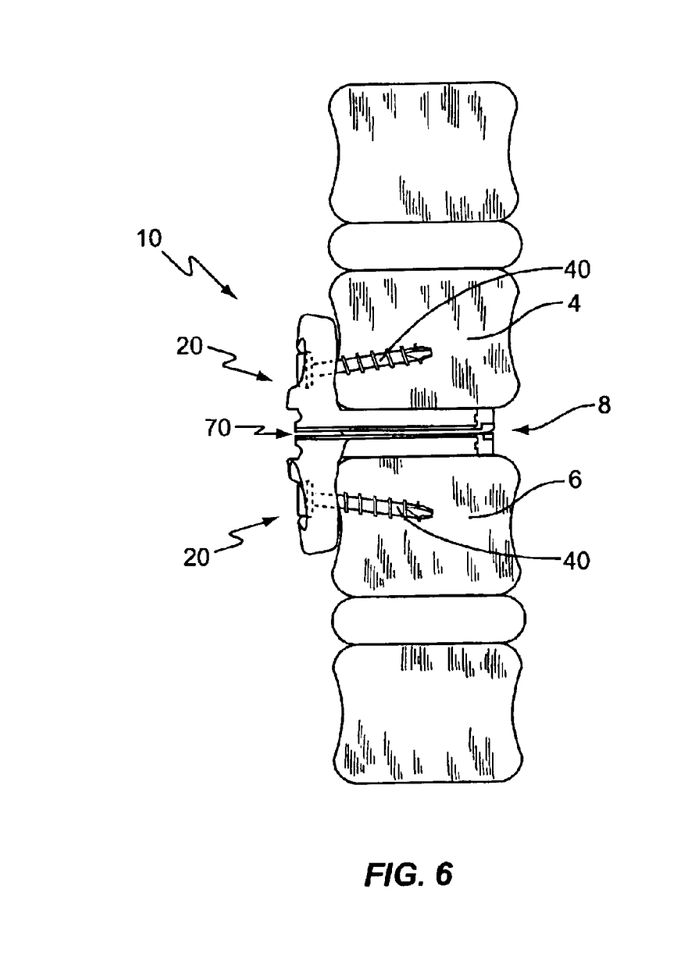
FIG. 6 shows the prosthesis system of FIG. 2 installed in a vertebral column.
Figure 7:
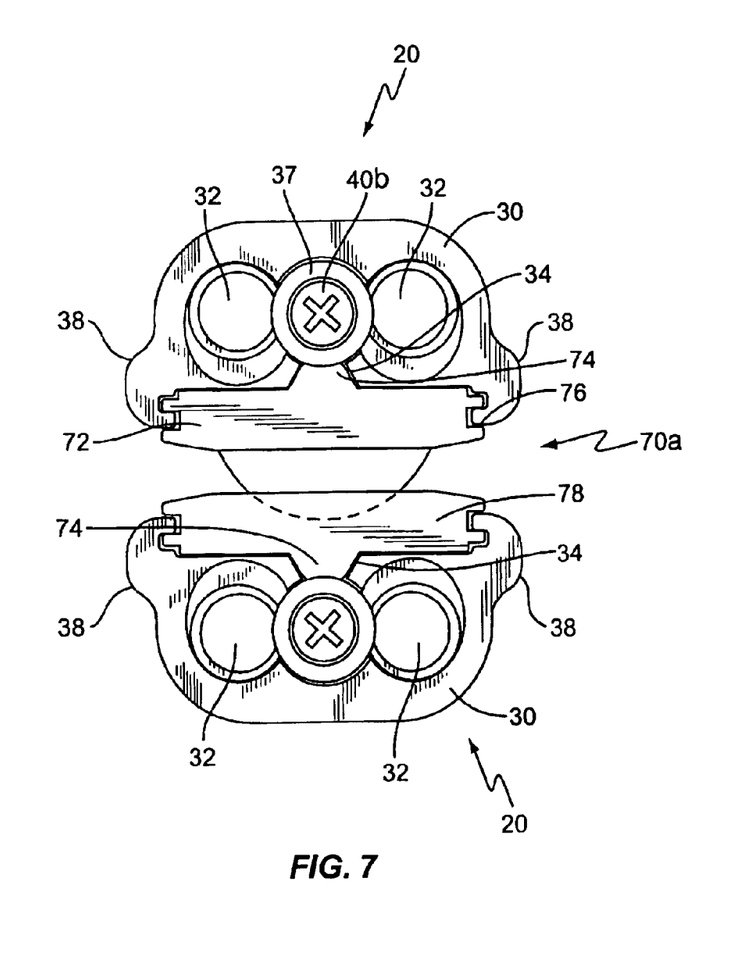
"FIG. 7 is a front view of an insert mounted between the baseplates."

Referring to FIG. 6, the prosthesis system 10 may be seen installed in the gap 8 between a superior vertebral member 4 and an inferior vertebral member 6. In the illustrated embodiment of the invention, the prosthesis 10 is inserted into the intervertebral disc space via an anterior approach; however, it should be understood that posterior and lateral approaches are also possible. With appropriate distraction applied to the vertebral members 4,6, one baseplate 20 is secured to the superior vertebral member 4 using screws 40a, and the other baseplate 20 is secured to the inferior vertebral member 6, likewise using screws 40a. With the baseplates 20 installed, the surgeon may chose to install either an articulating-type insert 70a or a fusion-type insert 70b; indeed, the decision as to which type of insert 70 to employ need not be made prior to the start of surgery, but may be delayed until the site has been examined during surgery. Assuming that an articulating-type insert 70a of the type shown in FIG. 2 is selected, the ball portion of the insert 72 may be slid into the baseplate 20 associated with the superior vertebral member 4 until tab 74 rests against notch 34. The retaining ring 37 may be placed in the recessed area of the mounting section 30, over the tip of the tab 74, and locking screw 40b inserted through the center of retaining ring 37 and into threaded hole 36. When screw 40b is fully threaded into hole 36, the retaining ring 37 urges the tab 74 firmly against the notch 34, thereby securing the ball portion 72 of the insert 70a to the corresponding baseplate 20. The other portion 78 of the insert 70a may then be mated to the other baseplate 20 in a similar fashion. Alternatively, both portions 72,78 of the insert 70a may be inserted into their respective baseplates 20 simultaneously, and thereafter locked in place via respective locking mechanisms (e.g., locking screw 40b and retaining ring 37). Thereafter, the surgical site is closed using conventional techniques.

It should be noted that the insert 70a is readily removable from the baseplates 20 immediately after installation. For the illustrated embodiments, the surgeon need only undo the locking mechanism, such as by removing locking screws 40b and retaining rings 37, and then slide the insert portions 72,78 out of engagement with the baseplates 20. With the first insert 70a removed, another insert 70a or 70b may be mated to the baseplates 20 without removing the baseplates 20 from the vertebral member 4,6. As such, the surgeon is free to try another an insert 70 of a different configuration (e.g., different in size, design, or type) in order to achieve the desired results. Indeed, the surgeon may initially try an articulating-type insert 70a, but then change to a fusion-type insert 70b without the need to install new baseplates 20, and during the same surgery. Once the proper insert 70 has been selected and installed, the surgeon may add an optional flexible or rigid element (not shown) secured to the exterior of mounting sections 30 of the two baseplates 20, if desired. If the optional element is flexible, it may function as an artificial ligament; if the optional element is rigid, it may function as a stabilizer.

One advantage of the present prosthesis system 10 is that it enables a fusion-type insert 70b to "see" the bone of the relevant vertebral members 4,6. That is, when to the insert 70b is installed in the baseplates 20, the insert 70b faces the bone through the aperture 60 of the corresponding baseplate 20. Over time, bone may grow through these apertures 60, "fusing" the insert 70b to the vertebral members 4,6. As such, while fusion-type inserts 70b may be readily removable immediately after installation, the insert 70b may become fixed in place over time. In order to promote this fusion process, the insert 70b may include appropriate ridges and/or pores on its end surfaces, and the insert 70b may include fusion promoting materials, as indicated above.

While the illustrative embodiments discussed above have assumed that the prosthesis system 10 replaces a single intervertebral disc, the present invention also encompasses situations where the prosthesis system 10 replaces more than one intervertebral disc—a so-called corpectomy construct. This can be achieved through the use of longer length inserts 70, or by having the insert 70 include an additional member acting as a substitute vertebral member between parts of the insert.

The discussion above has also described a situation where one insert 70 is installed, then removed and replaced with another insert 70 during the same surgery. However, the subsequent replacement may alternatively occur during a subsequent surgery, such as to replace a worn insert 70 or the like.

Additionally, although the devices and methods illustrated and described above are particularly useful in treating the cervical region of the spine, it should nevertheless be understood that the present invention is also applicable to other portions of the spine, including the lumbar or thoracic regions of the spine.

While the invention has been illustrated an described in detail in the drawings and foregoing description, the same is to be considered as illustrative and not restrictive in character. For instance, a different method of mounting the baseplates 20 to the vertebral members 4,6, such as using a different number of holes 32 and screws 40a and/or adhesives, may be employed if desired. Likewise, other locking mechanisms may be used to retain the inserts 70 in the baseplates 20, such as clips, snaps, of the like, and the retaining ring 37 may be integrated into the locking screw 40b if desired. It should therefore be understood that only some embodiments have been shown and described and that all changes and modifications that come within the meaning and equivalency range of the appended claims are intended to be embraced therein.

What is claimed is:

1. A modular intervertebral prosthesis assembly, comprising:
   a first baseplate having a first mounting section and a first intervertebral section extending away from said first mounting section, said first intervertebral section having a first aperture passing therethrough;
   a second baseplate having a second mounting section and a second intervertebral section extending away from said second mounting, said second intervertebral section having a second aperture passing therethrough;
   at least a first insert disposed between said first and second baseplates so as to face said first and second apertures and adapted to engage said first and second baseplates; and
   a retaining mechanisnm mounted to said first mounting section and on contact with said first insert to prevent the removal of said first insert from between said first and second baseplates, said retaining mechanism being spaced from said second baseplate such that said first insert is exposed between said first and second baseplates.

2. The assembly of claim 1 wherein said first and second baseplates have a generally L-shaped side profile.

3. The assembly of claim 1 wherein said first insert comprises a fusion element.

4. The assembly of claim 3 wherein said fusion element is selected from the group consisting of allograft bone and autograft bone.

5. The assembly of claim 1 wherein said first insert comprises an articulating insert.

6. The assembly of claim 5 wherein said first insert comprises at least two distinct members designed to move relative to one another after installation.

7. The assembly of claim 1 further comprising at least a second insert adapted to be disposed between said first and second baseplates so as to face said first and second apertures, said second insert of a different configuration than said first insert.

8. The assembly of claim 1 wherein said first insert connects to said first and second baseplates in a fashion so as to be removable therefrom immediately after installation.

9. The assembly of claim 8 wherein said first insert includes a rail and wherein said first intervertebral section comprises a groove for mating with said rail.

10. The assembly of claim 1 wherein said first intervertebral section comprises at least two arms extending away from to said first mounting section.

11. The assembly of claim 10 wherein said first intervertebral section further comprises a member bridging said arms and space from said first mounting section.

12. The assembly of claim 1 further comprising a plurality of fasteners for securing said mounting sections of said first and second baseplates to respective vertebral members.

13. The assembly of claim 1 wherein said first intervertebral section extends away from said first mounting section generally perpendicular thereto.

14. The assembly of claim 13 wherein said second intervertebral section extends away from said second mounting section generally perpendicular thereto.

15. The assembly of claim 1 wherein said first and second baseplates are interchangeable.

16. The assembly of claim 1 wherein:
   said first insert includes a rail;
   said first intervertebral section comprises at least two arms extending generally perpendicular away from said first mounting section and a groove for mating with said rail on said first insert;
   said first and second baseplates are interchangeable; and
   said first insert connects to said first and second baseplates in a fashion so as to be removable therefrom immediately after installation.

17. The assembly of claim 16 further comprising at least a second insert adapted to be disposed between said first and second baseplates so as to face said first and second apertures, said second insert of a different configuration than said first insert.

18. The device of claim 1, wherein said retaining mechanism comprises a screw having a head that extends over the first insert to prevent the insert from moving from between the first and second baseplates.

19. The device of claim 18, wherein the screw includes a retaining ring having a larger diameter than the head, the retaining ring extending over the first insert.

20. The device of claim 18, comprising a retaining ring having a central opening through which the screw extends and having a ring body that extends over the first insert.

21. The device of claim 1, further comprising a second retaining mechanism mounted to said second mounting section to prevent the removal of the first insert.

22. The device of claim 21, wherein the second retaining mechanism is spaced from said first baseplate such that the first insert is exposed between said first and second baseplates.

23. A modular intervertebral prosthesis kit, comprising:
a first baseplate having a first mounting section and a first intervertebral section extending away from said first mounting section, said first intervertebral section having a first aperture passing therethrough;
a second baseplate having a second mounting section and a second intervertebral section extending away from said second mounting, said second intervertebral section having a second aperture passing therethrough;
a first insert disposed between said first and second baseplates so as to face said first and second apertures and removably mated to said first and second baseplates;
a second insert adapted to be disposed between said first and second baseplates so as to face said first and second apertures when said first insert is unmated from said first and second baseplates, said second insert of a different configuration than said first insert; and
a retaining mechanism removably attached to the first baseplate, and on contact with the first insert to prevent removal of the first insert and the second insert when disposed between the first and second baseplates, the retaining mechanism sized to be spaced away from the second baseplate when mounted to expose the first insert and the second insert.

24. The assembly of claim 23 wherein said first intervertebral section comprises at least two arms extending away from to said first mounting section.

25. The assembly of claim 23 wherein said first insert comprises an articulating insert.

26. The assembly of claim 23 wherein one of said first and second inserts comprises an articulating insert and the other of said first and second inserts comprises a fusion insert.

27. The assembly of claim 23 wherein said first and second baseplates are interchangeable.

28. The device of claim 23, further comprising a tab that extends outward from the first insert, the tab contacting the first mounting section when the first insert is mounted between the first and second intervertebral sections to prevent over-insertion.

29. The device of claim 28, wherein one of the first mounting section comprises a recessed notch to receive the tab when the first insert is disposed between the first and second baseplates.

30. The device of claim 23, wherein the retaining mechanism comprises a screw sized to extend over the first insert and the second insert.

31. The device of claim 30, wherein the screw includes a retaining ring that extends outward from the screw to extend over the first insert and the second insert.

32. A modular intervertebral prosthesis assembly, comprising:
a first baseplate having a first mounting section and a first intervertebral section extending away from said first mounting section, said first intervertebral section having a first aperture passing therethrough;
a second baseplate having a second mounting section and a second intervertebral section extending away from said second mounting, said second intervertebral section having a second aperture passing therethrough;
at least a first insert disposed between said first and second baseplates proximate said first and second apertures and removably engaging said first and second baseplate; and
a screw mountable to one of the first and second mounting sections to retain the first insert within the first and second baseplates, the screw sized such that the first insert is exposed.

33. The assembly of claim 32 wherein said first insert comprises an articulating insert.

34. The assembly of claim 32 further comprising at least a second insert adapted to be disposed between said first and second baseplates when said first insert is disengaged from said first and second baseplates, said second insert of a different configuration than said first insert.

35. The assembly of claim 32 wherein said first and second baseplates have a generally L-shaped side profile.

36. The assembly of claim 32 wherein said first and second baseplates are interchangeable.

37. The assembly of claim 32, further comprising a ring attached to the screw, the ring sized to extend over the first insert.

38. A intervertebral prosthesis method, comprising:
providing a first baseplate having a first mounting section and a first intervertebral section extending away from said first mounting section, said first intervertebral section having a first aperture passing therethrough;
providing a second baseplate having a second mounting section and a second intervertebral section extending away from said second mounting section, said second intervertebral section having a second aperture passing therethrough;
securing said first baseplate to a superior vertebral member via said first mounting section;
securing said second baseplate to an inferior vertebral member via said second mounting section;
mating a first insert to said first and second baseplates, between the intervertebral sections thereof, such that said first insert faces said first and second apertures, said first insert being initially removably mated to said first and second baseplates; and
mounting a mechanism to the first baseplate and on contact with the first and retaining the first insert between the intervertebral sections while a front of the first insert remains exposed between the first and second mounting sections.

39. The method of claim further comprising removing said first insert and mating a second insert to said first and second baseplates, between the intervertebral sections thereof, such that said second insert views said first and second apertures.

40. The method of claim 38 wherein said first insert comprises a fusion element.

41. The method of claim 40 comprising fusing said fusion element to said superior and inferior vertebral members via said first and second apertures, respectively.

42. The method of claim 40 wherein said fusion element is selected from the group consisting of allograft bone and autograft bone.

43. The method of claim 38 wherein said first insert comprises an articulating insert.

44. The method of claim 38 further comprising:

unmating said first insert from said first and second baseplates;

thereafter mating a second insert to said first and second baseplates, between the intervertebral sections thereof, such that said second insert faces said first and second apertures, said second insert being initially removably mated to said first and second baseplates immediately after installation thereof.

45. The method of claim 44 wherein said second insert is of a different configuration than said first insert.

46. The method of claim 44 wherein said first insert comprises an articulating insert.

47. The method of claim 38, the step of retaining the first insert between the intervertebral sections comprises positioning a retaining ring over the first insert.

48. The method of claim 38, wherein the step of retaining the first insert between the intervertebral sections further comprises retaining securing members to one of the inferior or superior vertebral members.

49. A modular intervertebral prosthesis assembly, comprising:

a first baseplate having a first mounting section and a first intervertebral section extending away from said first mounting section, said first mounting section having a first aperture to receive a screw to attach the first baseplate to a first intervertebral member;

a second baseplate having a second mounting section and a second intervertebral section extending away from said second mounting;

an insert disposed between said first and second intervertebral sections; and a retaining mechanism attached to the first mounting section to prevent removal of the screw from the first intervertebral member and prevent removal of the insert from between the first and second intervertebral sections, the retaining mechanism sized such that the insert is exposed between the first and second baseplates.

50. The assembly of claim 49, wherein the retaining mechanism comprises a retaining screw that extends over the screw and the insert.

51. The assembly of claim 50, wherein the retaining mechanism comprises a retaining ring sized to extend over the screw and the insert.

52. The assembly of claim 49, further comprising a second aperture in the first mounting section to receive a second screw to attach the first baseplate to the first intervertebral member, the retaining mechanism sized to extend over the second screw.

53. A modular intervertebral prosthesis assembly, comprising:

a first baseplate having a first mounting section and a first intervertebral section extending away from said first mounting section, said first intervertebral section having a first aperture passing therethrough;

a second baseplate having a second mounting section and a second intervertebral section extending away from said second mounting, said second intervertebral section having a second aperture passing therethrough; and at least a first insert disposed between said first and second baseplates so as to face said first and second apertures and adapted to engage said first and second baseplates, the at least first insert further comprises an outwardly-extending tab that contacts one of the first and second mounting sections to prevent over-insertion when the first insert is positioned between the first and second baseplates.

54. The device of claim 53, wherein one of the first and second mounting sections comprises a recessed notch in which the tab contacts when the insert is positioned between the first and second baseplates.

55. The device of claim 53, further comprising a screw inserted within one of the first and second mounting sections, the screw having a head that extends over the tab to prevent the insert from moving from between the first and second baseplates.

56. The device of claim 55, wherein the screw includes a retaining ring having a larger diameter than the head, the retaining ring extending over the tab.

57. The device of claim 55, further comprising a retaining ring having a central opening through which the screw extends and having a ring body that extends over the tab.

58. The device of claim 53, further comprising a retaining mechanism for retaining the insert within the baseplates.

* * * * *